(12) United States Patent
Fabris et al.

(10) Patent No.: US 10,024,800 B2
(45) Date of Patent: Jul. 17, 2018

(54) GOLD NANOSTAR SUBSTRATES FOR SERS SENSING IN THE FEMTOMOLAR REGIME

(71) Applicant: Rutgers, The State University of New Jersey, New Brunswick, NJ (US)

(72) Inventors: Laura Fabris, Piscataway, NJ (US); A. Swarnapali D. S. Indrasekara, Houston, TX (US)

(73) Assignee: RUTGERS, THE STATE UNIVERSITY OF NEW JERSEY, New Brunswick, NJ (US)

( * ) Notice: Subject to any disclaimer, the term of this patent is extended or adjusted under 35 U.S.C. 154(b) by 0 days.

(21) Appl. No.: 15/304,246

(22) PCT Filed: Apr. 15, 2015

(86) PCT No.: PCT/US2015/025932
§ 371 (c)(1),
(2) Date: Oct. 14, 2016

(87) PCT Pub. No.: WO2015/160923
PCT Pub. Date: Oct. 22, 2015

(65) Prior Publication Data
US 2017/0045456 A1    Feb. 16, 2017

Related U.S. Application Data

(60) Provisional application No. 61/979,844, filed on Apr. 15, 2014.

(51) Int. Cl.
*G01N 21/65* (2006.01)
*B22F 9/24* (2006.01)
*C23C 14/16* (2006.01)
*C23C 30/00* (2006.01)

(52) U.S. Cl.
CPC ............. *G01N 21/658* (2013.01); *B22F 9/24* (2013.01); *C23C 14/16* (2013.01); *C23C 30/00* (2013.01); *G01N 2201/06113* (2013.01)

(58) Field of Classification Search
None
See application file for complete search history.

(56) References Cited

U.S. PATENT DOCUMENTS

| 2006/0046313 A1* | 3/2006 | Roth ................ G01N 33/54366 436/518 |
| 2008/0119832 A1* | 5/2008 | Cronin ................ A61B 5/0059 606/15 |
| 2010/0087723 A1 | 4/2010 | Van Duyne et al. |

(Continued)

FOREIGN PATENT DOCUMENTS

WO    2008028521 A1    3/2008

OTHER PUBLICATIONS

Khoury et al; "Gold Nanostars for Surface-Enhanced Raman Scattering: Synthesis, Characterization and Optimization", 2008, J. Phys. Chem. C, vol. 112, pp. 18849-18859.

(Continued)

*Primary Examiner* — Shawn Decenzo
(74) *Attorney, Agent, or Firm* — Fox Rothschild LLP

(57) ABSTRACT

The invention relates to Raman spectroscopy-based sensing technique. More particularly, the invention relates to a surface enhanced Raman spectroscopy (SERS) composite and methods of its use and fabrication.

21 Claims, 2 Drawing Sheets

(56) References Cited

U.S. PATENT DOCUMENTS

| | | |
|---|---|---|
| 2010/0284917 A1 | 11/2010 | Kustner et al. |
| 2011/0046018 A1 | 2/2011 | Chen et al. |
| 2011/0151586 A1* | 6/2011 | Chen .................... B22F 1/0062 |
| | | 436/531 |
| 2011/0168954 A1 | 7/2011 | Stevens |
| 2011/0267614 A1* | 11/2011 | Reinhard ............... B82Y 30/00 |
| | | 356/301 |
| 2013/0330815 A1 | 12/2013 | Van Duyne et al. |
| 2015/0177139 A1* | 6/2015 | Kim .................... G01N 21/554 |
| | | 356/445 |

OTHER PUBLICATIONS

Todorovic, et al: "Conformational Transitions and Redox Potential Shifts of Cytochrome P450 Induced by Immobilization", 2006, J. Biol Inorg Chem, vol. 11, pp. 119-127.

* cited by examiner

GOLD NANOSTAR SUBSTRATES FOR SERS SENSING IN THE FEMTOMOLAR REGIME

CROSS-REFERENCE TO RELATED APPLICATIONS

This application claims priority under 35 USC § 119(e) to U.S. Provisional Patent Application Ser. No. 61/979,844, filed on Apr. 15, 2014, which is hereby incorporated by reference in its entirety.

The present invention was made with government support under grant number DMR-1126468 awarded by the National Science Foundation. The United States government has certain rights in this invention.

FIELD OF THE INVENTION

The invention relates to sensing techniques based on surface enhanced Raman scattering (SERS) spectroscopy. More particularly, the invention relates to composites for SERS and their fabrication. In some embodiments, the invention relates to a SERS composite functionalized with Raman silent, primary amine-terminated, short alkanethiols, to which are in turn anchor capped gold nanostars.

BACKGROUND

Raman spectroscopy is a valuable analytical tool that employs characteristic vibrational patterns for the identification of molecules, but its direct implementation as a chemical sensing technique is limited due to the low scattering cross section of most Raman active molecules, which leads to low sensitivity. This limitation has been overcome by the discovery of surface enhanced Raman spectroscopy (SERS), which increases the intensity of Raman signals by leveraging the inherent and unique properties of plasmonic nanoparticles (NPs) hence leading to improved detection limits. The interaction of electromagnetic radiation with the oscillating cloud of conduction electrons of plasmonic nanoparticles results in electromagnetic energy confinement around the nanoparticles. By placing a Raman active molecule on or in close proximity to the nanoparticles, and hence within the confined electromagnetic field, it is possible to obtain significant Raman signal amplification. This phenomenon is known as SERS.

The design and fabrication of plasmonic nanoparticles to sustain high electromagnetic field enhancements for SERS have become a field of interest mainly in the analytical research community due to the high demand of ultrasensitive substrates for the detection of environmental pollutants, toxic industrial waste, and chemical warfare, to name a few. In SERS-based experiments, when a Raman active molecule (SERS reporter) is attached to a plasmonic NP, its Raman signal is boosted on average by about 5-6 orders of magnitude, with peaks of 8-10 orders of magnitude in non ensemble-averaged systems. It has been established that SERS signals can also be intensified via assembly of the plasmonic NPs into dimers and small clusters, where the local electromagnetic field enhancement increases by up to a value of $10^8$-$10^{10}$ at the junction between NPs, which is also known as the "SERS hot spot." In addition, high confinement of the electromagnetic energy has also been reported to be present at the sharp edges or tips of anisotropic nanoparticles such as nanorods, nanocubes, and nanoprisms, which have also been widely studied and reported in literature as superior SERS substrates.

Recently, star-shaped gold nanoparticles (spherical core structures with protruding sharp tips) have emerged as excellent SERS substrates, where extraordinary field confinement and enhancement can be observed at the acute tips, that can thus act as excellent "hot spots". (Khoury, C. G. et al. *J. Phys. Chem. C* 2008, 112, 18849; incorporated herein by reference in its entirety). The optical properties of nanostars have also been found to be strongly dependent on the morphology of the protruding tips. (Alvarez-Puebla, R., Liz-Marzan, L. M.; Garcia, d. A. *J. Phys. Chem. Lett.* 2010, 1, 2428; incorporated herein by reference in its entirety). This excellent structure-optical property relationship in gold nanostars has been exploited to design substrates for chemical- as well as bio-detection.

Top-down and bottom-up techniques have been equally utilized for the fabrication of SERS substrates. Many elegant NP substrates have been presented with reproducible large-scale periodic arrays by using, for example, electron beam lithography and focused-ion beam lithography. However, the implementation of top-down methods is limited by the high fabrication cost and the constraints in the inter-nanoparticle space tunability necessary to achieve maximum field enhancements. These limitations can be circumvented by bottom-up procedures that are much cheaper and offer flexibility in controlling the inter-nanoparticle spacing, particularly for NP-assembly-guided SERS substrates, easily reaching inter-nanoparticle separations as low as 1 nm. Bottom-up approaches also permit the use of anisotropic NPs, like gold nanostars and nanorods, which exhibit excellent plasmonic properties with size tunability.

Similar to the top-down methods, SERS platforms prepared from the bottom-up can and should be well characterized for quantitative data acquisition, and designed with high reliability and reproducibility by careful and controlled fabrication practices. Successful implementations of these advantageous features are evident in the variety of emerging bottom-up designed SERS substrates with superior SERS enhancement.

Most of the nanoparticle fabrication methods for SERS-based chemical sensing applications have followed the "sandwich architecture", where a narrow gap between nanoparticles or nanoparticles and a plasmonic film is created, to take advantage of the quantum confinement effect. For example, in fabrication of a bottom-up approach, dithiolated analyte molecules are sandwiched between a gold film and gold nanostars, and enable zeptomolar sensitivity in the detection of 1-naphthalenethiol. However, in practice, this approach limits its use only to dithiolated analytes. A modified version of this approach was reported for the detection of non-functionalized analytes with limits of detection up to $10^{-5}$ M. It was reported that the SERS spectrum for such analytes could only be acquired when they were positioned exactly at the junction between the nanostar tips and the gold thin film. This criterion however would be hard to implement in ultrasensitive detection regimes, thus limiting their widespread use. Not only star-shaped nanoparticles but also other anisotropic nanoparticles, fabricated to give rise to quantum confinement effects, have been used in the literature for SERS-based chemical detection.

Even though these approaches have been able to address the detection of different types of analytes, a solution that overcomes the above-described inadequacies and shortcomings is still needed in the engineering of SERS substrates, particularly for ultrasensitive detection of non-functionalized analytes.

SUMMARY

Having recognized the shortcomings of the prior art, the present invention provides a novel composite for SERS and methods for its use and fabrication.

One aspect of the invention provides a composite for surface enhanced Raman spectroscopy (SERS) comprising nanoparticles immobilized to a substrate via $C_{2-10}$ alkyl linkers. The linkers form linkages with the substrate and the nanoparticles through —NH—, —S—, —O—, or —COO—. The nanoparticles include nanospheres having an average diameter in the range of about 10-100 nm and protrusions on the nanosphere surface.

In some embodiments, the substrate includes silicon, polymer, glass, silicon nitride, quartz, ceramics, sapphire, metal, or combination thereof. In some embodiments, the substrate includes silicon and a coating of a metal selected from the group consisting of gold, silver, aluminum, copper, platinum, and alloy thereof. In some embodiments, the substrate and the nanoparticles include gold.

In some embodiments, the protrusions on the nanospheres are in the shape of tips. In some embodiments, the tips have an average height in the range of about 5-150 nm. In some embodiments, each of the nanoparticles include about 5-50 tips.

In some embodiments, one or more carbons of the linker are replaced with an aryl or a cycloalkyl. In some embodiments, the linker is derived from 1-thio-6-amino-hexane.

In some embodiments, the linkage to the substrate includes —S— and the linkage to the nanoparticles includes —NH—.

Another aspect of the invention provides a device comprising the composite of the present invention. In some embodiments, the device further includes a laser source having an excitation wavelength in the range of about 100 nm to about 1000 nm.

Another aspect of the invention provides an enhanced SERS method for detecting a substance comprising
a) contacting a composition with the nanoparticles of the present invention;
b) exposing the nanoparticles to a laser having an excitation wavelength ranging from about 100 nm to about 1000 nm; and
c) detecting the emission of a Raman spectrum indicative the amount or presence of the substance in the composition.

In some embodiments, the excitation wavelength of the laser overlaps with a plasmon resonance peak of the nanoparticles. In some embodiments, the excitation wavelength of the laser and a plasmon resonance peak of the nanoparticles are less than about 50 nm apart.

In some embodiments, the method further includes adjusting the concentration of the composition and detecting the opposite changes in intensity for at least two peaks of the emission spectrum, wherein an increase in intensity of a peak accompanied by a decrease in intensity of another is indicative of the presence of the substance in the composition.

Another aspect of the invention provides a method of producing a composite for SERS, comprising
(a) coating a substrate with a metal, wherein the metal is selected from the group consisting of gold, silver, aluminum, copper, platinum, and alloy thereof;
(b) providing a plurality of nanoparticles, wherein said nanoparticles comprise nanospheres having an average diameter in the range of about 10-100 nm and protrusions in the shape of tips on the surface of the nanospheres; and
(c) immobilizing said nanoparticles to the substrate via a plurality of C2-10 alkyl linkers, wherein said linkers form linkages to the substrate and the nanoparticles selected from —NH—, —S—, —O—, and —COO—.

In some embodiments, the method further includes blocking the active sites on the substrate surface with a blocking agent after step (c).

In some embodiments, the protrusions on the nanoparticles comprise tips, said tips prepared by contacting nanospheres with a coating solution, wherein the seed volume and the concentration of the coating solution are adjusted to control the shape and quantity of the tips.

In some embodiments, the tips are prepared by contacting nanospheres with a coating solution, wherein the seed volume and the concentration of the coating solution are adjusted to control the shape and quantity of the tips.

Another aspect of the invention provides a composite produced according to the above described method.

DETAILED DESCRIPTION

Figure 1:
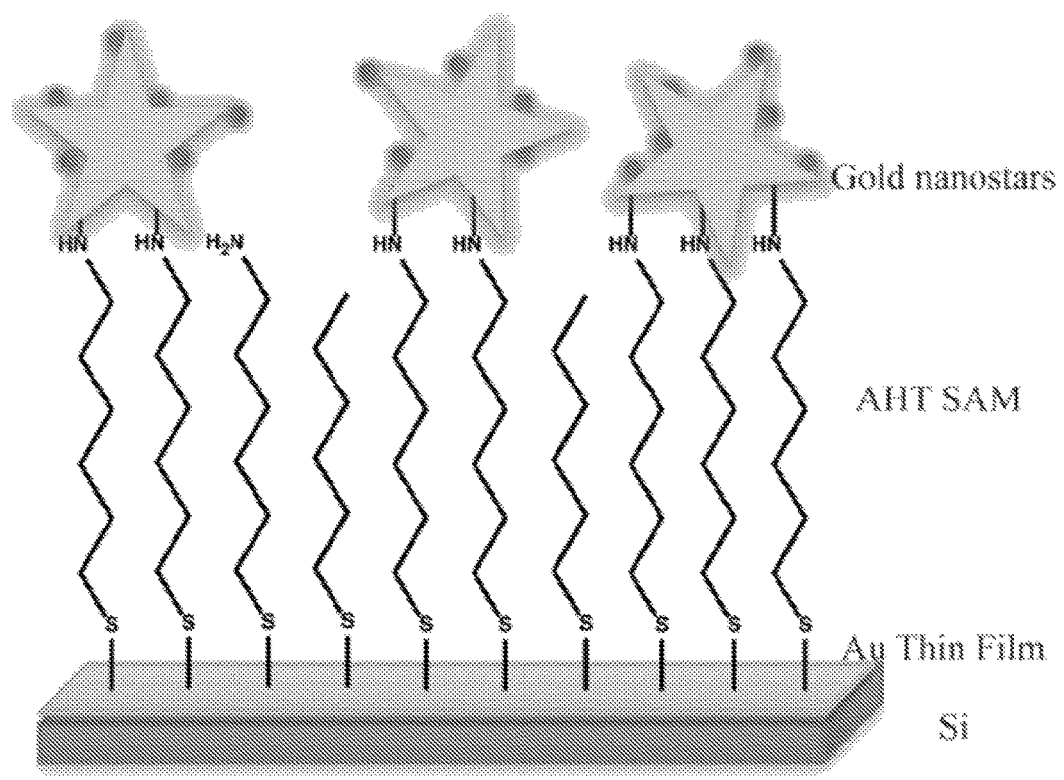
FIG. 1 is a schematic representation of the composite used for SERS-based detection.

Various embodiments of the invention provide novel composites for detection of chemisorbed or physisorbed substances/analytes. The composites offer flexible detection of substances with high sensitivity and reproducibility regardless of their chemical affinity towards nanoparticles of the composites.

Throughout this patent document, various publications are referenced. The disclosures of these publications in their entireties are hereby incorporated by reference into this application in order to more fully describe the state of the art to which the disclosed matter pertains. While the following text may reference or exemplify specific elements of a composite or a method of utilizing the composite, it is not intended to limit the scope of the invention to such particular reference or examples. Various modifications may be made by those skilled in the art, in view of practical and economic considerations, such as the size and sharpness of the tips and the linkers as SAMs.

The articles "a" and "an" as used herein refers to "one or more" or "at least one," unless otherwise indicated. That is, reference to any element or component of the present invention by the indefinite article "a" or "an" does not exclude the possibility that more than one of the element or component is present.

The term "about" as used herein refers to the referenced numeric indication plus or minus 10% of that referenced numeric indication.

The term "nanoparticle" as used herein generally refers to a particle that exhibits one or more properties not normally associated with a corresponding bulk material (e.g., quantum optical effects, etc.). The term also generally refers to materials having at least two dimensions that do not exceed about 1000 nm. And, in various embodiments described herein, these dimensions are even smaller.

The term "nanoparticle" as used herein refers to a solid particle ranging from about 1 nm to about 1,000 nm in length, width, or diameter. The term includes nanorods, nanospheres, nanocones, nanorectangles, nanopyramids, nanoprisms and other geometric shapes. Non-limiting examples of nanoparticles include solid noble metal nanoparticles or alloys thereof and are about 1 to about 800 nm in at least one dimension and have surface plasmon absorption (and scattering) in the visible-near infrared region of the spectrum.

The term "noble metal" refers to metals such as gold, silver, or copper. Nanoparticles of noble metals, such as Ag, Au, and Pt, may be used in preparation of plasmonic nanoparticles. Any metal may be used in the metal nanoparticles in various embodiments, such as gold, silver, copper and aluminum, or some combination.

Composite for High Sensitivity Detection

One aspect of the invention provides a composite for SERS-based high sensitivity detection. The composite includes a substrate tethered to nanoparticles via a linker. The point of linkage to the substrate and nanoparticles can be any suitable moieties including for example amino and thio (—S—) group. The size and shape of the nanoparticles are critical in surface-enhanced Raman scattering spectra. In particular, the nanoparticles of the present invention feature protrusions on the surface, which contribute to the enhanced detection of a variety of substances or analytes.

Various types of materials are suitable as a substrate of the composite. Non-limiting examples include silicon, polymers, glass, silicon nitride, quartz, ceramics, sapphire, and metals and combination thereof. In some embodiments, the substrate is a silicon wafer. The substrate may be coated with a noble metal such as gold, silver, copper, aluminum, platinum or alloy thereof, which contributes to eliminate any SERS enhancement due to the surface roughness that could interfere with the substance detection. Preferably, the coating has a smooth surface. The thickness of the coating may range from about for example about 1 nm to about 300 nm, all subunits included. Exemplary embodiments of the thickness of the coating include about 1, 5, 10, 20, 40, 60, 80, 100, 120, 140, 160, 180, 200, 250 and 300 nm. In some embodiments, the substrate comprises a coating of gold, which also provide reactive sites for the linker to bind to via linages such as amino or thio groups.

The nanoparticles of the composite may be composed of various materials. In some embodiments, the nanoparticles include at least a noble metal such as aluminum, copper, silver, platinum or gold. In some embodiments, the nanoparticles include alloys such as copper/silver/gold alloy (e.g., copper-silver alloy, copper-gold alloy, silver-gold alloy, copper-silver-gold alloy). In some embodiments, the nanoparticles include a core of, for example silica, platinum, or other metal particles, onto which a layer is deposited, e.g., layers of Cu, Ag, or Au. In some embodiments, the nanoparticles include gold. In some embodiments, the nanoparticles include copper. In some embodiments, the nanoparticles include silver. In some embodiments, the nanoparticles include platinum.

The frequency and intensity of a plasmon resonance of nanoparticles are generally determined by the intrinsic dielectric property of a given metal, the dielectric constant of the medium in contact with the metal, and the pattern of surface polarization. As such, any variation in the shape or size of a metal particle that can alter the surface polarization and causes a change to the plasmon resonance. This dependence offers the ability to tune the surface plasmon resonance, or localized surface plasmon resonance (LSPR) of metal nanoparticles through shape-controlled synthesis. Accordingly, nanoparticles can be prepared in various sizes and shapes to fine tune the surface polarization and plasmon resonance in SERS. Non-limiting examples of the shapes include spherical (nanospheres), cube shape (nanocubes), rod shape (nanorod) or wire shape (nanowires).

In some embodiments, the nanoparticles have a sphere shape (nanospheres) with protrusions on the surface thereof. The shapes of these nanoparticles can be obtained by various nanoparticle synthesis methods known in the art without undue experiments. For example, gold nanostars with different shapes and plasmonic properties can be synthesized by changing the seed volume and concentration of HAuCl4.

In each of these shapes, the nanoparticle will have an effective average diameter, which as used herein is the smallest cross-section of the nanoparticle or the plasmon-resonating portion thereof, e.g., a plasmon-resonating layer. Generally, the plasmon-resonating nanoparticles should have an effective average diameter of about 1, 5, 10, 20, 30, 40, 50, 60, 70, 80, 90, 100, 150, 200, 250, 300, 350, 400, 450, 500, 550, 600, 650, 700, 750, 800, 850, 900, 950, 1000 nm. In some exemplary embodiments, the average diameter is in the range of about 10-20, 10-30, 10-40, 10-50, 10-60, 10-70, 10-80, 10-90, or 10-100 nm, all subunits included. The wavelength of light plasmon-resonated by the nanoparticles will vary with the size and shape of the nanoparticles.

The density of the nanoparticles on the substrate may vary depending on factors such as the substances to be detected and the production process for the nanoparticles. Non-limiting examples of nanoparticle density include about 10-800 particles/$\mu m^2$, all subunits and sub-ranges included. Other examples include about 20, 40, 60, 80, 100, 120, 140, 160, 180, 200, 250, 300, 350, 400, 450 and 500 particles/$\mu m^2$.

The nanoparticles include protrusions of various shapes on the surface to further modify the plasmonic resonance properties of the nanoparticles. For example, the protrusion may be in the shape of columns, cones, tips, ridges, or combination thereof. In some embodiments, the protrusions are tips and the nanoparticles are shaped like nanostars.

Figure 2A:
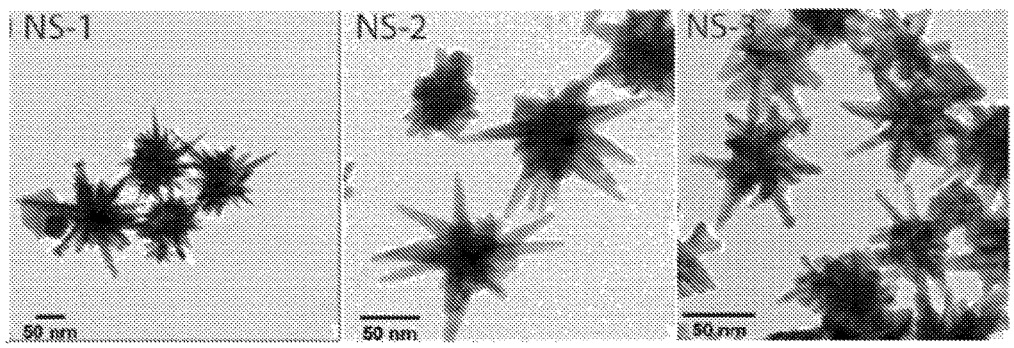
FIG. 2A illustrates the transmission electron microscopy images of gold nanostars of varying tip morphology.
Figure 2B:
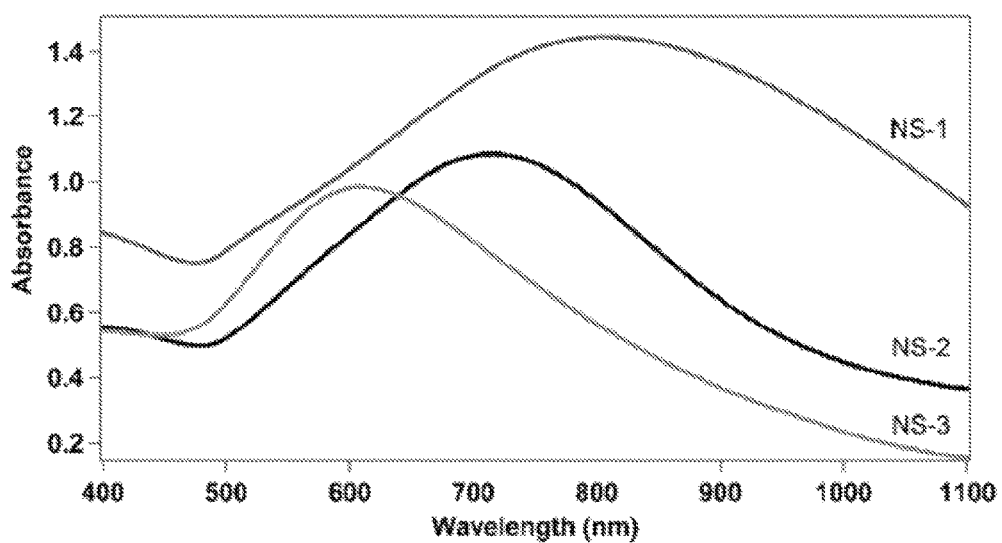
FIG. 2B illustrates UV-visible spectra of gold nanostars.

SERS is affected by various attributes/parameters of the tips, including number of cones per nanoparticle, the height and the sharpness of the tips. The tips can be made from the same or different material from the nanospheres. In some embodiments, the tips contain one or more noble metals as described above (e.g. Au, Ag, and Pt). In some embodiments, the tips are composed of gold. The correlation between the tip morphology and plasmonic properties are illustrated in FIGS. 2A and 2B. FIG. 2A shows the transmission electron microscopy images of nanostars, which include nanoparticles with tips in various, density sizes and sharpness. FIG. 2B shows the corresponding UV-visible spectra of the nanostars.

The sharpness of the tips can be defined by the radius of curvature at the tip end. In some embodiments, the radius of curvature at the tip ranges from about 1 nm to about 200 nm. Non-limiting examples of the radius of curvature for the cone tip include about 0.5, 1, 2, 3, 4, 5, 6, 7, 8, 9, 10, 15, 20, 25, 30, 35, 40, 45, 50, 55, 60, 65, 70, 75, 80, 85, 90, 95, 100, 110, 120, 130, 140, 150, 160, 170, 180, 190 and 200 nm. Because the tips may or may not be in the shape of a perfect cone, a single tip likely has multiple radii of curvature at the tip end.

The height of the tips ranges from about 1 nm to about 200 nm. Non-limiting examples of cone height include about 1, 2, 3, 4, 5, 6, 7, 8, 9, 10, 15, 20, 25, 30, 35, 40, 45, 50, 55, 60, 65, 70, 75, 80, 85, 90, 95, 100, 110, 120, 130, 140, 150, 160, 170, 180, 190 and 200 nm.

The overall structure of the nanoparticle can be further defined by the ratio between the diameter of the nanosphere (not including the cone on the surface) and the height of the cone. Generally, the ratio ranges from about 100:5 to about 20:100, all subunits and sub-ratios included. Non-limiting examples of the ratio include about 10:1, 9:1, 8:1, 7:1, 6:1, 5:1, 4:1, 3:1, 2:1, 1:1, 1:2, 1:3, 1:4, and 1:5.

Greater SERS intensity can be achieved with self-assembled monolayers (SAMs) attached to the substrate. In the present invention, the linker that tethers the substrate and the nanoparticles serves the role of SAMs. Various types of SAMs are known in the art. For example, SAMs can be derived from functionalized alkanes, which bear groups such as —NH2, —SH, OH, and —COOH at the terminal positions. The resulting linkages therefore include moieties such as —NH— (amino), —S—, —O—, and —COO—. In some embodiments, the linkage to the substrate is —S—. In some embodiment, the linkage to the substrate is amino group which can be substituted with a group such as a $C_{1-10}$ alkyl. Exemplary alkyl contain 1, 2, 3, 4, 5, 6, 7, 8, 9, or 10 carbons. In some embodiments, one or more carbons of the alkane may be replaced with an optionally substituted aryl group (e.g phenyl and tolyl) or cyclo-$C_{3-8}$ alkyl. In some embodiments, the composite comprises one or more different types of functionalized alkanes as SAMs.

A blocking agent can be used on the substrate surface to prevent non-specific interactions between analyte molecules and the substrate, which would interfere with the SERS analysis. Suitable blacking agents include, for example, Raman silent organic molecules with thio or amino groups that will form a chemical bond with the substrate surface. In some embodiments, the blocking agent is a thiol-containing $C_{1-10}$ alkane. In some embodiments, the blocking agent is hexane-1-thiol.

Another aspect of the invention provides a device or kit containing the above described composite. The device or kit may further include a light source which is able to produce wavelengths in the range of 100-1000 nm. In some exemplary embodiments, the light source produces wavelengths in the ranges of 150 nm to 800 nm, 200 nm to 750 nm, 300 nm to 700 nm, 400 nm to 700 nm, 450 nm to 700 nm, 450 nm to 650 nm, or 550 nm to 700 nm. In some embodiments, the light source is a UV source producing UV light having a wavelength of from 100 nm to 400 nm. In some embodiment, the light source produces one or more wavelengths, sequentially or simultaneously.

The device or kit may further include a detector for detecting the Raman signal of the analyte. Characteristics of the Raman signal include wavelength, range, number and intensity of peaks.

Method of Detection

Another aspect of the present invention provides a method of detecting the amount or presence of an analyte or substance in a composition, comprising: contacting the composition to be detected with the above described composite, wherein the analyte or substance, if present, is chemisorbed or physisorbed to the nanoparticles of the composite; exposing the nanoparticle-bound analyte or substance to an excitation wavelength; and detecting the Raman signal. Key indicators or parameters of the Raman signal include for example wavelengths and intensity of the emission peaks. The detection method of the present invention finds broad applications in areas including particle measurement, process control, and environmental monitoring.

The method of the present invention can be applied to the detection various types of analytes, substances or compositions for authenticity, concentration or integrity. In some exemplary embodiments, the method include the following steps: depositing the composition to be detected to the nanoparticles; exposing the composition to one or more excitation wavelengths, sequentially or simultaneously; detecting the Raman signal of the composition; comparing the key indicators of the Raman signal with that of a reference signal or spectrum to determine the presence, amount, concentration and integrity of the composition.

The method may also include the step of adjusting the concentration of the tested composition. A decrease in concentration for an analyte or substance may lead to re-orientation of the analyte or substance molecules with respect to the metal surface in order to maximize the molecular interaction. As a result of the altered molecular interaction, the peak intensity in Raman signal is increased and/or decreased. In some exemplary embodiments, a change in concentration may lead to an increase in intensity for a peak, which is accompanies by the decrease in intensity for another peak. Because the rate and extent of the re-orientation depends on the specific molecular structure as well as the concentration of a particular analyte or substance, detection of the change in intensity can be used in the confirmation of an analyte's identity. Non-limiting examples of the concentrations of the tested substance or composition ranges from about 10 nM to 1000 nM, all subunits and sub-ranges included. Exemplary embodiments for the concentration include equal or less than about 10, 20, 30, 40, 50, 60, 70, 80, 90, 100, 120, 140, 160, 180, 200, 250, 300, 400, 500, 600, 700, 800, 900, and 1000 nM.

The excitation wavelength ranges from 100-1000 nm as described above. The excitation wavelength and the plasmon resonance peaks may overlap or separate from each other. In some embodiments, the excitation wavelength overlaps with the plasmon resonance band of the nanoparticles. In non-limiting examples, the excitation wavelength is apart from a plasmon peak of nanoparticles by about 2, 5, 10, 15, 20, 35, 30, 35, 40, 50, 60, 70, 80, 90 or 100 nm. The power of the laser excitation is adjustable depending on factors such as the plasmon properties of the nanoparticles and the substance to be detected. Non-limiting examples of the power include from about 10 µW to about 1000 µW, all subunits and sub-ranges included.

The analyte, substance or composition to be tested is exposed to the laser source for a sufficient period of time to generate a Raman signal. In some exemplary embodiments, the period of time ranges from less that about 1 second to about 3 hours.

The analyte or substance may be chemisorbed or physisorbed to the nanoparticles. An analyte or substance is chemisorbed to the nanoparticles when chemical bonding is involved. For example, 4-mercaptobenzoic acid (4-MBA) may be immobilized through the chemical bonding of the thio-moeity of 4-MBA to metal surface of the nanoparticles. An analyte or substance may also be physisorbed to the nanoparticles by means other than chemical bonding. In the example of crystal violet (CV), the molecules may be immobilized via its highly conjugated π system which interacts with the nanoparticle surface via van der Waals force. An analyte or substance may also be immobilized on the metal surface by both chemisorption and physisorption. Although two examples of analytes are described in the example section, those skilled in the art would understand that the type of analyte or substance detected by the disclosed SERS substrate is not particularly limited and may also include melamine, sulfamerazine; carbaryl, tricyclazole and paraquat among others.

In order to enhance the detection of the Raman signal, the analyte or substance may also be functionalized to include various functional groups. The functional groups serve to immobilize the analyte, improve its stability, or provide other signal enhancement benefit. For example, an analyte or substance may be modified to incorporate a thiol group or a π system for immobilization. Meanwhile, a reactive group may be shielded by known protecting groups (e.g. FMOC for amino group). Introduction of the appropriate groups can be determined by one of ordinary skill in the art without undue experiments.

The analyte, substance or composition to be tested may be disposed to the nanoparticles in various forms. In some exemplary embodiments, the analyte, substance or composition is disposed to the nanoparticle surface in a powder, a vapor, or a solution or suspension.

Another advantage of the detection method lies in the multiplexing ability of the nanoparticles. Two or more substances may be attached to the nanoparticles via chemisorption and/or physisorption simultaneously. For example, crystal violet (CV) and 4-MBA can be detected as a mixture.

Method of Production

Another aspect of the invention provides a method of producing a composite for surface enhanced Raman spectroscopy (SERS), comprising immobilizing nanoparticles to a substrate via a plurality of $C_{2-10}$ alkyl linkers, wherein said linkers comprises linkages to the nanoparticles and the substrate selected from —NH—, —S—, —O—, and —COO—, said nanoparticles comprise protrusions on the surface thereof, and said nanoparticles and said substrate comprise a coating of noble metal.

The substrate and nanoparticles are as described above. The substrate may include a coating of a metal such as gold, silver, copper and platinum. In some embodiments, the coating has a smooth coating to prevent signal interference. The nanoparticles are composed of metals or alloys as described above.

The preparation of nanoparticles with protrusions on the surface can be accomplished through various methods known in the art (see for example, Yuan, et al., Nanotechnology, 2012, 23, 075102; Bastus, et al., Langmuir, 2011, 27, 11098-11105; U.S. Pat. No. 8,808,420). In an exemplary embodiment, citrate capped spheres are added to a coating solution and mixed thoroughly by stirring. A solution of reducing agent is subsequently added. After a desirable period of time, nanoparticles with protrusions can be purified by for example centrifugation. The metal in the coating solution may vary depending upon the desired plasmon properties of the nanoparticles. In some embodiments, the coating solution contains $HAuCl_4$. The selection of reducing agent in association with the metal to be coated is generally known in the art. In some embodiments, the reducing agent is ascorbic acid, used in combination with $AgNO_3$ to produce a coating of gold. The shape and density of the protrusions on the nanoparticles can be controlled by adjusting the seed volume and concentration of the coating solution. For example, the protrusions may be cones or tips with different sizes and sharpness, which can be controlled with suitable seed volume and concentration of the coating solution. The density of the cones or tips on the nanoparticles may also be modified similarly. The specific sharpness of the tips or cones can be defined by the radius of curvature at the end of the tip end or the top of the cone as described above. Complete cones, including right circular cones and oblique circular cones are defined as a shape including a base and a lateral surface, wherein the lateral surface is formed by the locus of all straight line segments joining the apex to the perimeter of the base. The cones prepared according to the present invention include complete cones and partial cones. Partial cones meet the definition complete cones partially at the base, lateral surface or the apex but bear other structural features such as a truncated lateral surface or cone tip and an uneven lateral surface. Tips may have the structures of complete or partial cones.

Immobilization of the nanoparticles on the substrate generally requires a self-assembled monolayer which is a linker comprising functional groups connecting the substrate and the nanoparticles. In an exemplary embodiment, a substrate is first coated with a noble metal (e.g. gold, silver, copper, platinum, or alloy thereof). The metal-coated substrate is then exposed to the linker, whereby linkages (e.g. —NH—, —S—, —O—, and —COO—) are formed between the linker and the substrate. In some embodiments, the linkage between the linker and the substrate comprises —S—. The linker can be an alkyne functionalized with groups such as aryl and halogen. One or more carbons of the linker may be replaced by a ring or aryl group. In some embodiments, the linker is 1-thio-6-amino-hexane.

Before the nanoparticles are attached to the other end of the linker, the substrate surface may be blocked with a blocking agent to prevent non-specific binding of the analyte molecules to the metal surface of the substrate. Non-limiting examples of the blocking agent include —SH, —NH, —OH, and —COOH terminated, substituted or unsubstituted, alkanes. In some embodiments, the blocking agent is 1-thio-hexane. In some embodiments, the linkage between the substrate and the linker is a thio group. In some embodiments, the linkage between the linker and the nanoparticles is an amino group. The SAMs comprising the linker is then incubated with for example, colloidal suspensions of nanoparticles. The density of the nanoparticles immobilized on the substrate can be modified by varying the concentration of the nanoparticles.

Also provided is a composite produced according to the above described method. Such a composite finds applications in the detection of various analytes due to its excellent SERS enhancement effect, multiplexing capability and low-cost fabrication.

EXAMPLES

Example 1

Gold nanostars (NS) with plasmon peak maxima at 620 nm (NS-1), 720 nm (NS-2), and 830 nm (NS-3) were synthesized according to a modified version of the surfactant-free nanostar synthesis. Briefly, 20 μL of 1 N HCl and 25 μL of 12 nm citrate capped spheres (A=2.81) were added to 10 mL of 1 mM $HAuCl_4$ solution and mixed thoroughly by stirring. Then 200 μL of 100 mM ascorbic acid and 400 μL of 3 mM $AgNO_3$ were simultaneously added to the above mixture, gently stirred for 7 min, and purified by centrifugation at 3000 g for 15 min. As purified gold nanostars (NS-1) were resuspended in 10 mL of MiliQ water and refrigerated until further use. Gold nanostars with different plasmonic properties were synthesized by changing the seed volume and concentration of $HAuCl_4$. In particular, the same procedure was followed with 25 μL of seeds to synthesize NS-2, and with 10 mL of 0.4 mM $HAuCl_4$ to synthesize NS-3. The plasmon properties of the nanostars are illustrated in FIGS. 2A and 2B. The syntheses of ~36 nm (SP-36) and ~130 nm (SP-130) in diameter citrate capped gold nanospheres were carried out according to the protocols published by Bastus et al. (Langmuir 2011, 27, 11098; incorporated herein by reference in its entirety).

Hydrogen tetrachloroaurate (HAuCl4.3H2O), trisodium citrate, ascorbic acid, silver nitrate, 6-aminohexane-1-thiol (AHT), hexane-1-thiol (HT), 4-mercaptobenzoic acid (4-MBA), dibenzene-4-thiol (DBT), and crystal violet (CV) were purchased from Sigma Aldrich. Si (110) wafers were purchased from University Wafers Inc. Ultrapure MiliQ water was used for all the syntheses. All the glassware was cleaned with aqua regia followed by MiliQ water and air-dried before used.

Example 2

This example illustrates the immobilization of nanoparticles on substrates. A schematic representation of the gold nanoparticle (NP) substrates is shown in FIG. 1. Si substrates of 0.5×0.5 cm2 surface area were cleaned with methanol, acetone, water, and hydrofluoric acid in the given order. Air-dried Si substrates were then sputter coated with a smooth 60 nm thick layer of gold. Atomic force micrographs (AFM) of Au thin films on Si substrates prior to NP deposition provide evidence of a smooth Au surface (RMS=0.282 nm) (see FIG. 4). The presence of a smooth Au surface is important in order to eliminate any SERS enhancement due to the surface roughness that could interfere with the analyte detection.

The gold-coated Si substrates were then immersed in 4 mM ethanolic solution of AHT for 24 hrs to form a self-assembled monolayer (SAM) followed by thorough rinsing with ethanol and air-drying. Next, the smooth gold substrates were incubated with 1 mM HT (blocking agent) for 24 hrs, rinsed with ethanol and air-dried. Any remaining empty sites on the gold substrates will be occupied by HT thereby preventing non-specific binding of analyte molecules onto the bare gold substrate. As prepared SAMs of AHT were then incubated with colloidal suspensions of gold nanoparticles for 48 hrs followed by rinsing with MiliQ water. Samples were prepared by using varying concentrations of gold nanoparticles (500 µL of 0.5 nM, 1.0 nM, and 3 nM) in order to coat the substrates with varying nanoparticle densities. Gold nanostars and nanospheres were both used for substrate preparation. The thiol moiety of AHT covalently binds to the gold substrate while its pendant primary amine group covalently binds to the nanoparticles. As prepared gold nanoparticle-coated substrates were then incubated with varying concentrations of analyte molecules for 24 hrs followed by thorough rising with ethanol. Ethanolic solutions of 4-MBA (100 µM to 10 fM), ethanolic solutions of CV (100 µM to 1 pM), and a mixture of ethanolic 4-MBA and DBT in THF (100 µM to 1 pM) were used as the analytes of interest. All the samples were air-dried before analysis.

AFM images of NP-coated substrates provide conclusive evidence of the immobilization of the nanoparticles of interest on the substrates. Helium ion microscopy (HIM) images were acquired to calculate the nanoparticle surface coverage, that is the density of nanoparticles present in a given field of view. 3 nM SP-130 substrates present a surface density of 150 spheres/µm2 with 30% particle aggregation while 3 nM NS-1 substrates have an average surface density of 110 stars/µm2 with 20% aggregates. The micrographs also show that the nanostar surface coverage increases as the concentration of the nanoparticle suspension increases.

Example 3

Gold nanostars (NS) with plasmon peak maxima at 620 nm (NS-3), 720 nm (NS-2), and 830 nm (NS-1) were analyzed to understand the effect of NS morphology on SERS enhancement factors (EF) and thereby on the detection sensitivity (see FIGS. 2A and 2B). The UV-vis spectra were recorded on a Nanodrop 3000 spectrometer (Thermo Scientific). The morphology of the nanoparticles was evaluated by using a Topcon 002B transmission electron microscope, and size information was extracted using the Image J software. Nanoparticle substrates were characterized for surface coverage and aggregation by an ORION™ Helium Ion Microscope (Carl Zeiss SMT), and atomic force microscope (Digital instrument nanoscope iii). All the Raman and SERS spectra of analyte solutions and nanoparticle substrates were obtained using a Reinshaw inVia Raman microscope.

Among these nanostars, there is a distinct difference in the number of tips per nanoparticle and the sharpness of the tips, where NS-1 possesses more tips with a higher sharpness while NS-3 has relatively shorter and less sharp tips. The spherical core of the NS is equivalent to a sphere of 36±3 nm in diameter while the outer diameter of the NS (that is the imaginary sphere that can be drawn by connecting the outermost atoms on the tips) equals 130±6 nm. Therefore gold nanospheres of 36 nm and 130 nm in diameter were synthesized and analyzed to compare the SERS EF and detection limits of gold nanospheres to those of NS.

Example 4

The applicability of the gold nanostar substrates for quantitative chemical detection was demonstrated by SERS analysis of 4-MBA as the model molecule. 4-MBA is a Raman active molecule with a relatively low scattering cross-section, which can chemisorb to Au nanoparticles via its pendant thiol moiety as well as through $\pi$ system interaction. SERS analysis is also used (a) to determine the lowest detection limit that can be achieved using the nanostar substrate, and (b) to compare the effectiveness and SERS EF of nanostars over nanospheres for SERS-based chemical sensing (proof-of-concept experimentation).

The SERS spectra for gold nanostar substrates were obtained using a 785 nm diode laser excitation (166 µW, spot size 1 mm) while 633 nm HeNe laser excitation (492 µW, spot size 1 mm) was used for nanosphere-coated substrates with single accumulation for 10 s acquisition time under a 50× objective. SERS spectra and intensities presented here are the averages of five baseline-corrected measurements obtained at random places on the samples. SERS intensities of the samples are normalized to the response of an internal reference (i.e. the intensity of Si peak at 512 cm−1) and reported here as I SERS/I Ref. For SERS mapping, 20×20 µm2 areas on the samples were raster-scanned at 2 µm step size under the same acquisition conditions reported above.

In an exemplary Raman spectrum of an ethanolic solution of 50 mM 4-MBA, the characteristic peaks associated with ring breathing modes at 1074 cm−1 and 1582 cm−1 were identified along with the band at 1070 cm−1 corresponding to C═O stretching vibrations of non-dissociated carboxylic groups. For SERS analysis, the NP substrates were incubated with varying concentrations of ethanolic 4-MBA from 1 mM to 10 fM, and the SERS intensity at 1077 cm−1 was recorded. Both nanosphere and nanostar substrates show a nearly linear trend between the SERS response and the concentration of 4-MBA, where the SERS response decreases as the concentration of 4-MBA decreases. It should be noted that the trend line was drawn only to guide the reader towards the concentration dependence of SERS response, and it is not meant to be an interpolation. This linear trend is more prominent at lower analyte concentrations (below 10 µM), which could be attributed to the presence of a single monolayer of analyte molecules atop the nanoparticles (instead of several monolayers that could be generated at higher concentrations). These data provide a strong evidence to support the use of the disclosed SERS substrates in quantitative SERS-based chemical sensing. The SERS signature of 4-MBA was detectable at 1 pM for all the NS samples. On the other hand, the lowest detection limit for 4-MBA on citrate-capped gold nanospheres of 36 nm in diameter (SP-36) and 130 nm in diameter (SP-130) substrates was limited to 10 nM under the same experimental conditions. This observation supports the concept that a higher SERS enhancement is exhibited by NPs with sharp tips over their spherical counterparts (proof-of-concept experimentation). For NS-1 substrates, the most sensitive of the set, SERS analysis at a much lower concentration regime was carried out. It revealed that 10 fM of 4-MBA is the lowest SERS detection limit achievable with this substrate with a good signal-to-noise ratio (S/N=3.8), which is equivalent to 900 molecules (see below for a detailed calculation) in the laser beam spot. As the concentration of 4-MBA decreases, the SERS responses were localized only at certain locations but not all over the substrate. Interestingly, as the probing concentration of 4-MBA decreases below 100 nM, it can be noticed that the relative intensity of the SERS peak at 1077 cm−1 decreases while the peak at 715 cm−1 increases. The ring-breathing mode at 1077 cm−1 is a characteristic of 4-MBA when it is bonded to Au through S in a nearly upright position. The peak at 715 cm−1 arises due to the out-of-plane C—C—C bending mode, which appears when the molecule is sitting parallel to the Au surface. This observation suggests that as the analyte concentration decreases, the orientation of the analyte with respect to the Au surface alters so as to maximize the molecular interaction, which is reflected by peak pattern changes in the SERS spectra.

Example 5

The SERS enhancement of 4-MBA on the nanoparticle substrates was calculated by considering the intensity at 1077 cm−1, and using the following equation:

$$EF=[I_{SERS}]/[I_{Raman}] \times [N_{Raman}]/[N_{SERS}]$$

The SERS intensity (ISERS) at 1 pM 4-MBA for NS substrates and 10 nM 4-MBA for nanospheres substrates was considered for SERS EF calculations. Since a patchy distribution of SERS signal was observed at the lowest detectable 4-MBA concentration on NS substrates (10 fM), we decided to consider 1 pM 4-MBA treated NS substrates for accurate estimation of EF, where a monolayer coverage of analytes over nanoparticles can be ensured. The average Raman intensity for 50 mM ethanolic 4-MBA was considered for IRaman. NRaman was calculated as the number of 4-MBA molecules present in the laser spot size. In order to calculate NSERS within the laser spot size, it was assumed that a monolayer of 4-MBA molecules exists all over the SERS substrate. Knowing the analyte surface coverage and the surface area irradiated by the laser excitation, the number of probed 4-MBA molecules was calculated using the following equation: NSERS=(Molar Surface coverage of the analyte×Avogadro's number×lasers spot size). The SERS EFs for 4-MBA on the test substrates are tabulated in the Table 1. According to the calculations, NS substrates showed SERS enhancements that are 4 orders of magnitude higher than those calculated for substrates coated by Au nanospheres of corresponding size. This can be mainly attributed to morphological differences, where the sharp tips of star-shaped nanoparticles act as SERS "hot spots". However, in this experiment, we did not address all the tips individually with suitable polarized light. Instead, we assumed that analyte molecules are distributed all over the nanostar surface rather than being concentrated at the tip. It should also be noted that the claimed approach in designing SERS substrates did not utilize the external "quantum confinement effect" and therefore the observed SERS EF can be correlated to the particle morphology itself. Under the given conditions, the calculated SERS EF for nanostar substrates, 109, is very reasonable and close to theoretical predictions (Kumar, P. S., Pastoriza-Santos, I., Rodriguez-Gonzalez, B., De Abajo, F. Javier Garcia; Liz-Marzan, L. M. Nanotechnology 2008, 19, 015606; incorporated herein by reference in its entirety), and it is anticipated that even larger SERS EFs could be achieved under optimized conditions. Under 785 nm laser excitation, the SERS EF for the disclosed NS substrates is 3-4 order of magnitudes higher than the values reported by Yuan et. al (4×105) and Lee et. al (2.7×106) for gold nanostars. (Nanoscale 2014, 6, 616; incorporated herein by reference in its entirety). This can be attributed to the presence of much sharper tips and no polymer or thick surfactant coating in the disclosed nanostars.

TABLE 1

Calculated SERS EF for 4-MBA on gold nanoparticle substrates.

| Substrate | Average SERS EF |
|---|---|
| 3 nM NS-1 | $4.9 \times 10^9$ |
| 3 nM NS-2 | $1.6 \times 10^9$ |
| 3 nM NS-3 | $5.3 \times 10^8$ |
| 3 nM SP-36 | $6.7 \times 10^4$ |
| 3 nM SP-130 | $1.2 \times 10^5$ |

The observed difference in SERS EF for different nanostars explains the importance of the laser excitation source in achieving the maximum electromagnetic enhancement. It is well known that having plasmon resonance peaks overlapping with the laser excitation wavelength leads to maximized surface plasmon responses and can thereby yield the maximum SERS EF that can be achieved for a given NP.

The plasmon peak for NS-1 is located at around 800 nm (see FIG. 2B), which is very close to the laser excitation wavelength (785 nm). This resonance gives a significant contribution to the observed EF for NS-1, in comparison to what seen for NS-3 where the laser excitation is slightly off-resonance with the plasmon peak located at 630 nm.

The variation of SERS response for 4-MBA depends on the NS-1 density on the SERS substrate. Regardless of the NS-1 densities on the substrates (28 particles/μm2 Vs 110 particle/μm2), the SERS EF lies within the same order of magnitude (109). This observation suggests that, in the absence of major clustering and aggregation, the morphology of nanoparticles plays a more important role in the SERS effect than the surface coverage levels herein considered do.

In practice, unlike 4-MBA, most analyte molecules do not possess thiol moieties that can facilitate chemical interactions with gold nanoparticle substrates. In order to understand the capability of the disclosed substrates to detect physisorbed, rather than chemisorbed, analyte molecules, a set of experiments was carried out with 3 nM NS-1 substrates for crystal violet (CV) as the model analyte. CV can interact with Au NPs through its highly conjugated π system, which is weaker in comparison to the chemical bonding that occurs with 4-MBA. Aqueous solutions of CV at neutral pH show a maximum absorption at 590 nm.

Therefore, in order to avoid the resonance Raman effect and to accurately estimate the signal enhancement, all the SERS measurements for CV samples were carried out under 785 nm laser excitation. Even without chemical bonding between nanostars and CV, NS-1 substrates were able to detect CV at a concentration as low as 1 pM with a SERS EF of 1.1×108. This suggests the applicability of the disclosed nanostar-based SERS substrates for analyte molecules that lack chemical affinity towards gold. These observations also explain the importance of considering the mode of interaction of the analyte with the nanoparticle in claiming the SERS EF for a given nanoparticle substrate.

The quantitative multiplexing ability of NS substrates was also studied by treating the 3 nM NS-1 substrates with a mixture of 4-MBA and DBT. A characteristic vibrational mode of DBT at 1279 cm−1 was used along with the peak at 1077 cm−1 for 4-MBA to selectively identify the presence of each analyte on the SERS substrate. The presence of both 4-MBA and DBT can be clearly detected at a concentration as low as 1 pM.

It will be appreciated by persons skilled in the art that the present invention is not limited to what has been particularly shown and described. Rather, the scope of the present invention is defined by the claims which follow. It should further be understood that the above description is only representative of illustrative examples of embodiments. The description has not attempted to exhaustively enumerate all possible variations. The alternate embodiments may not have been presented for a specific portion of the invention, and may result from a different combination of described portions, or that other un-described alternate embodiments may be available for a portion, is not to be considered a disclaimer of those alternate embodiments. It will be appreciated that many of those un-described embodiments are within the literal scope of the following claims, and others are equivalent. Furthermore, all references, publications, U.S. patents, and U.S. patent application Publications cited throughout this specification are incorporated by reference as if fully set forth in this specification.

The invention claimed is:

1. A composite for surface enhanced Raman spectroscopy (SERS) comprising nanoparticles immobilized to a substrate via a plurality of $C_{2-10}$ alkyl linkers, wherein said linkers comprise linkages bonding to the substrate and the nanoparticles via functional groups selected from the group consisting of —NH—, —S—, O, and COO—, one or more carbons of the linker is optionally replaced with an aryl or a cycloalkyl, and said nanoparticles comprise nanospheres having an average diameter in the range of about 10-100 nm and protrusions on the nanosphere surface, further wherein there is no polymer or surfactant coating on the nanoparticles.

2. The composite of claim 1, wherein the substrate comprises silicon, polymer, glass, silicon nitride, quartz, ceramics, sapphire, metal, or combination thereof.

3. The composite of claim 1, wherein the substrate comprises silicon and a coating of a metal selected from the group consisting of gold, silver, copper, platinum, an alloy of two or more thereof, aluminum, and an alloy of aluminum and copper.

4. The composite of claim 1, wherein the substrate and the nanoparticles comprise gold.

5. The composite of claim 1, wherein protrusions comprise tips.

6. The composite of claim 5, wherein the tips have an average height in the range of about 5-150 nm.

7. The composite of claim 5, wherein each of the nanoparticles comprise about 5-50 tips.

8. The composite of claim 5, wherein the ratio between the average diameter of the nano spheres and the average height of the tips is in the range of from about 2:1 to about 1:5.

9. The composite of claim 1, wherein one or more carbons of the linker is replaced with an aryl or a cycloalkyl.

10. The composite of claim 1, wherein the linker is derived from 1-thio-6-amino-hexane.

11. The composite of claim 1, wherein the linkage to the substrate comprises —S— and the linkage to the nanoparticles comprises —NH—.

12. A device comprising the composite of claim 1.

13. The device of claim 12, further comprising a laser source having an excitation wavelength in the range of about 100 nm to about 1000 nm.

14. A SERS method for detecting a substance in a composition comprising
   a) contacting said composition with the nanoparticles of claim 1;
   b) exposing the nanoparticles to a laser having an excitation wavelength ranging from about 100 nm to about 1000 nm; and
   c) detecting the emission or lack thereof of a Raman spectrum indicative of the amount or presence of the substance in the composition.

15. The method of claim 14, wherein the excitation wavelength of the laser overlaps with a plasmon resonance peak of the nanoparticles.

16. The method of claim 14, wherein the excitation wavelength of the laser and a plasmon resonance peak of the nanoparticles are less than about 50 nm apart.

17. The method of claim 14, further comprising adjusting the concentration of the composition and detecting the presence or absence of opposite changes in intensity for at least two peaks of the emission spectrum, wherein an increase in intensity of a peak is accompanied by a decrease in intensity of another in the emission spectrum is indicative of the presence of the substance in the composition.

18. A method of producing a composite for SERS, comprising
   (a) coating a substrate with a metal, wherein the metal is selected from the group consisting of gold, silver, copper, platinum, an alloy of two or more thereof, aluminum, and an alloy of aluminum and copper;
   (b) providing a plurality of nanoparticles, wherein said nanoparticles comprise nanospheres having an average diameter in the range of about 10-100 nm and protrusions on the surface of the nanospheres, further wherein there is no polymer or surfactant coating on the nanoparticles; and
   (c) immobilizing said nanoparticles to the substrate via a plurality of $C_{2-10}$ alkyl linkers, wherein said linkers bond to the substrate and the nanoparticles via functional groups selected from —NH—, —S—, —O—, and —COO—.

19. The method of claim 18, further comprising blocking the active sites on the substrate surface with a blocking agent after step (c).

20. The method of claim 18, wherein the protrusions on the nanoparticles comprise tips, said tips prepared by contacting nanospheres with a coating solution, wherein the seed volume and the concentration of the coating solution are adjusted to control the shape and quantity of the tips.

21. A composite for SERS produced according to claim 18.

* * * * *